(12) United States Patent
Wehling et al.

(10) Patent No.: US 9,724,391 B2
(45) Date of Patent: *Aug. 8, 2017

(54) COMBINATION PREPARATION INCLUDING A CORTICOSTEROID AND EXOSOMES

(75) Inventors: Peter Wehling, Düsseldorf (DE); Julio Reinecke, Köln (DE)

(73) Assignee: ORTHOGEN AG, Düsseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/142,573

(22) PCT Filed: Dec. 10, 2010

(86) PCT No.: PCT/EP2010/069426
§ 371 (c)(1),
(2), (4) Date: Sep. 27, 2011

(87) PCT Pub. No.: WO2011/082950
PCT Pub. Date: Jul. 14, 2011

(65) Prior Publication Data
US 2012/0237587 A1 Sep. 20, 2012

(30) Foreign Application Priority Data
Dec. 10, 2009 (DE) .......................... 10 2009 057 495

(51) Int. Cl.
| | | |
|---|---|---|
| A61K 35/14 | (2015.01) | |
| A61K 38/20 | (2006.01) | |
| A61K 9/127 | (2006.01) | |
| A61P 19/02 | (2006.01) | |
| A61P 29/00 | (2006.01) | |
| A61P 19/04 | (2006.01) | |
| A61P 25/00 | (2006.01) | |
| A61P 37/00 | (2006.01) | |
| A61P 17/14 | (2006.01) | |
| A61K 31/573 | (2006.01) | |
| A61K 45/06 | (2006.01) | |
| A61K 35/15 | (2015.01) | |
| A61K 35/19 | (2015.01) | |
| A61K 9/00 | (2006.01) | |
| A61K 9/51 | (2006.01) | |
| A61K 38/00 | (2006.01) | |

(52) U.S. Cl.
CPC ............ *A61K 38/20* (2013.01); *A61K 31/573* (2013.01); *A61K 35/15* (2013.01); *A61K 35/19* (2013.01); *A61K 45/06* (2013.01); *A61K 9/0014* (2013.01); *A61K 9/0019* (2013.01); *A61K 9/5184* (2013.01); *A61K 38/00* (2013.01); *A61K 2300/00* (2013.01)

(58) Field of Classification Search
None
See application file for complete search history.

(56) References Cited

U.S. PATENT DOCUMENTS

| | | | |
|---|---|---|---|
| 2,793,159 A | * | 5/1957 | Johnson ............... A61K 31/573 514/178 |
| 6,713,246 B1 | | 3/2004 | Reinecke |
| 2006/0116321 A1 | | 6/2006 | Robbins et al. |

FOREIGN PATENT DOCUMENTS

| | | | |
|---|---|---|---|
| CN | 101022824 | | 8/2007 |
| EP | 0 343 684 A1 | | 5/1989 |
| JP | 2008505104 | | 2/2008 |
| WO | WO 00/46249 | | 8/2000 |
| WO | WO 03/080122 A1 | | 10/2003 |
| WO | WO-2006-007529 | * | 1/2006 |
| WO | WO 2006/007529 A2 | | 1/2006 |
| WO | WO2007/008155 | | 1/2007 |

OTHER PUBLICATIONS

Barry Bresnihan, et. al.:"Treatment of Rheumatoid Arthritis with . . . " in: Arthritis & Rheumatism, Dec. 12, 1998.
Lucas D. Settas, et. al.: "Reativation of Pulmonary Tuberculosis . . . ", in: Journal of Clinical Rheumatology, Aug. 4, 2007.
Nicole R. Bianco et. al.: "Therapeutic Effect of Exosomes from Indoleamine . . . " in:Arthritis & Rheumatism, Feb. 2009.
F. U. Hornstein: "Orthokotin . . . ", in: Arznei-Telegramm, No. 3 2001.
Hoffmann, E.A., et al., "Regulation of myocillin-associated exosome release from human trabecular meshwork cells", Invest. Ophthalmol. Vis. Sci., Mar. 2009, 50(3):1313-8.
Xiang, X., et al., "Induction of myeloid-derived suppressor cells by tumor exosomes", Int. J. Cancer, Jun. 1, 2009; 124(11):2621-33.
Jiang, Y. et al, "A multicenter, double-blind, dose-ranging, randomiyed, placebo-controlled study of recombinant human interleukin-1 receptor antagonist in patients with rheumatoid arthritis: . . . ", Arthritis Rheum., May 2000; 43(5):1001-9.
Chang, K.H., et al., "Treatment of severe alopecia areata with intralesional steroid injections", J. Drugs Dermatol, Abstract, Oct. 2009; 8(10):909-12.
Burmester, G.-R. et al. "Naglyandnaya lmmunologiya", Moscow: BINOM. Laboratoriya Ynanii, 2007, p. 214.A.
YB Philippovich:Osnovy biokhimii [Fundamentals of Biochemistry]Publishing house "High School", Moscow, 1969,p. 492.

(Continued)

*Primary Examiner* — Frederick Krass
*Assistant Examiner* — Celeste A Roney
(74) *Attorney, Agent, or Firm* — Ursula B. Day

(57) ABSTRACT

The present invention relates to pharmaceutical compositions for a combination therapy with a corticosteroid and exosomes. By means of the combination therapy diseases such as osteoarthritis, arthritis and/or degenerative spinal diseases can be treated.

28 Claims, 1 Drawing Sheet

(56) References Cited

OTHER PUBLICATIONS

Khimicheskaya Entsiklopedia [Chemical encyclopedia] vol. 2; Ed. by I.L. Knunyants;Publishing house "Sovetskaya Entsiklopedia", Moscow, 1990;p. 958.
MA Mashkovskii:Lekarstvennye sredstva [Drugs] (Manual for Physicians), Part 1, Twelfth edition, revised and enlarged; Moscow, "Medicine", 1993; p. 664-666.

* cited by examiner

COMBINATION PREPARATION INCLUDING A CORTICOSTEROID AND EXOSOMES

CROSS-REFERENCES TO RELATED APPLICATIONS

This application is the U.S. National Stage of international Application No. PCT/EP2010/069426, filed Dec. 10, 2010, which designated the United States and which claims the priority of German Patent Application, Serial No. 10 2009 057 495.6, filed Dec. 10, 2009, pursuant to 35 U.S.C. 119(a)-(d).

BACKGROUND OF THE INVENTION

Field of the Invention

The present invention relates to pharmaceutical compositions for a combination therapy with a corticosteroid and exosomes. By means of the combination therapy diseases such as osteoarthritis, arthritis and/or degenerative spinal diseases can be treated, wherein the treatment is preferably carried out locally.

Technical Background

Osteoarthritis in Germany refers to "joint wear" to a higher degree than typical for a certain age. It is accompanied by a loss of cartilage in the respective joint, which results in pain and function deterioration. Excess strain, congenital or traumatic causes such as joint malpositions or also bone deformation through bone diseases like osteoporosis are viewed as causes. It can also result from another disease such as joint inflammation or accompany effusion caused by excess strain.

Generally all joints can be affected by osteoarthritic changes. In Germany the disease is most frequently located in the knee joint. Osteoarthritis is one of the most common reasons for seeking advice at a general practitioner's practice. Approximately 10% of the population in Western countries suffer from osteoarthritis. If osteoarthritis diseases of the small vertebral joints and the degenerative intervertebral disc diseases are added, even approx. 15%-20% of the population are affected. The risk of suffering from osteoarthritis increases with age. About two thirds of people over 65 years are affected by the disease, however, not all persons affected also suffer from the symptoms.

For the treatment of osteoarthritis some therapy forms are already known. This includes conservative (e.g. medicinal) therapies as well as surgical procedures to the point of replacing the complete joint by a prosthesis. In order to avoid these extensive and irreversible interventions, an effective medicinal treatment is generally preferred to delay the point in time of a complete joint replacement as far as possible.

However, many medicinal treatments also have disadvantages. On the one hand this is due to the side effects of the medicaments themselves, but their effects are also partially limited.

A medicinal agent frequently used for treating osteoarthritis and rheumatoid arthritis is cortisone (also applied locally) and related corticosteroids. These are administered systemically in the case of RA and locally as an injection into the affected joint in the case of osteoarthritis. However, it is found that the positive effect of a corticosteroid administration in osteoarthritis as well as rheumatoid arthritis already significantly decreases after just one week. This is clinically proven by randomized studies and clinical experience. In RA it is tried by continuous administration of cortisone to systemically keep a high level of the agent, however this is problematic due to an increase of side effects and reduction of the therapeutical effect in continuous administration.

Exosomes are small vesicles coated by a lipid membrane, which are found in the extracellular space for example of the human body. They are formed and secreted by cells by separation from the cellular plasma membrane. Normally these exosomes also contain proteins which they have adopted from their original cell. Methods for the preparation and administration of exosomes are described for example in patent application WO 2006/007529 A2. In in vitro induction of prophylactically or therapeutically effective proteins such as e.g. IL-1Ra by incubation of a blood sample in an appropriate vessel such as e.g. a syringe, exosomes are formed. Consequently, Orthokine for example contains exosomes. The formation of exosomes may be increased by means of adding an additive which stimulates the formation of exosomes. The concentration of exosomes may be increased by centrifugation with high centrifugal forces, for example. The use of exosomes in the treatment of rheumatoid arthritis is known per se.

A further medicament which can be used for treating osteoarthritis is the protein IL-1Ra, which is produced naturally in the body, or an isoform or fragment thereof, which shows a similar activity. Interleukin-1-receptor antagonist (IL-1Ra) binds to the same receptors on the cell surface as interleukin-1 (IL-1), but does not trigger the signaling cascade normally caused by IL-1Ra binding. By binding to the IL-1 receptor, IL-1Ra blocks the binding of IL-1 and thus prevents its transduction of signals and thus the inflammatory effect of IL-1 on the target cells.

Treatment of patients with autologous serum in which IL-1Ra was enriched, is known in the state of the art. IL-1Ra used in this way is also called Orthokine. A recombinant IL-1Ra fragment, Anakinra, in contrast did not show any effects in the treatment of osteoarthritis compared to a placebo treatment. Anakinra is an isoform of the human interleukin-1 receptor antagonist shortened to amino acids 26-177 and terminally L-methionylated and has a sequence length of 153 amino acids. The preparation is done for example by means of *Escherichia coli* strains using recombinant methods.

In the light of the state of the art, the problem to be solved was thus to provide a medicinal treatment of osteoarthritis, which is more effective and particularly shows a good long-term efficacy. The treatment should furthermore preferably have a good efficacy, preferably long-term efficacy, in arthritis, particularly rheumatoid arthritis.

SUMMARY OF THE INVENTION

Surprisingly it was now found that the efficacy, in particular the long-term efficacy and rapidness of onset of efficacy of corticosteroids such as cortisone in osteoarthritis, arthritis and degenerative spinal diseases, can be significantly or synergistically improved by additional administration of exosomes. This is particularly found when locally administering the therapeutics into the joint to be treated. One of the surprising findings is for example that the use of corticosteroids in combination with exosomes, which were obtained for example in an Orthokine syringe from a blood sample (e.g. corticosteroid together with Orthokine), regarding rapidness of onset of efficacy in osteoarthritis, seems to be superior to a therapy not comprising the agent exosomes. A rapid onset of efficacy can also be observed if exosomes are added as an additional agent to an already effective osteoarthritis therapy (such as corticosteroid together with Anakinra).

The combination of corticosteroid and exosomes also shows a strikingly good efficacy in the treatment of rheumatoid arthritis concerning the rapidness of onset of efficacy as well as the long-term efficacy. An especially advantageous effect was shown due to a surprisingly high efficacy (due to the different pathophysiological approaches) together with a particularly favourable side effect profile for the patient. The favourable side effect profile is of particular importance, as the chronic administration of corticosteroid is linked to significant side effects such as metabolic irregularities, osteoporosis and other side effects. By combining exosomes with corticosteroids such as cortisone, however, the unfavourable effects of the corticosteroids (the cortisone) are reduced and the efficacy of the treatment is increased.

Regardless of the indication, it could be observed in many patients that the combination of exosomes with corticosteroids shows a therapeutic effect exceeding the sum of the single therapeutic effects of the two agents exosomes and corticosteroids, particularly if not both agents are therapeutically effective when administered on their own.

Thus, the present invention in a first aspect provides a pharmaceutical composition comprising a corticosteroid together with exosomes in the presence or absence of a cytokine antagonist and/or a growth factor.

The expression "absence of a cytokine antagonist" in the scope of the present invention means that not a single cytokine antagonist is present. This applies to the growth factor mutatis mutandis.

The pharmaceutical composition according to the first aspect in each case comprises a corticosteroid and exosomes. Furthermore there is either the option of the presence or the option of the absence of a cytokine antagonist; additionally there is either the option of the presence or the option of the absence of a growth factor.

The therapeutics may also be administered in two different pharmaceutical compositions simultaneously or sequentially. Accordingly, the invention in a second and third aspect provides a pharmaceutical composition comprising exosomes in the presence or absence of a cytokine antagonist and/or a growth factor for use in a combination therapy together with a corticosteroid as well as a pharmaceutical composition comprising a corticosteroid in the presence or absence of a cytokine antagonist and/or a growth factor for use in a combination therapy together with exosomes.

The invention in a fourth aspect provides a pharmaceutical composition comprising a cytokine antagonist and/or a growth factor for use in a combination therapy together with a corticosteroid and exosomes.

In a fifth aspect according to the invention a kit is provided comprising (i) a pharmaceutical compostion comprising exosomes in the presence or absence of a cytokine antagonist and/or a growth factor and (ii) a pharmaceutical composition comprising a corticosteroid in the presence or absence of a cytokine antagonist and/or a growth factor.

Furthermore the invention in a sixth aspect relates to the use of exosomes in the presence or absence of a cytokine antagonist and/or a growth factor for the preparation of a pharmaceutical composition for use in a combination therapy together with a corticosteroid, and in a seventh aspect the use of a corticosteroid in the presence or absence of a cytokine antagonist and/or a growth factor for the preparation of a pharmaceutical composition for use in a combination therapy together with exosomes.

The combination therapy mentioned above in relation to the second, third, fourth, sixth and seventh aspect is preferably a combination therapy together with a cytokine antagonist and/or a growth factor, particularly in the cases where a cytokine antagonist and/or a growth factor is absent from the pharmaceutical composition itself.

In an eighth aspect the present invention relates to a method for preparing a pharmaceutical composition comprising a corticosteroid and exosomes comprising the steps: providing a blood sample containing exosomes, preferably concentrating the exosomes and mixing with a corticosteroid.

Further embodiments of the invention are mentioned in the following detailed description and in the claims.

DESCRIPTION OF THE INVENTION

The invention is based on the surprising finding that the treatment of joint and spinal diseases such as osteoarthritis, arthritis and degenerative spinal disease as well as autoimmune diseases such as neurodermitis and alopecia areata by means of corticosteroids can be significantly improved by additional administration of exosomes. Thus the invention is directed towards the combination therapy of such diseases by means of a corticosteroid together with exosomes. It may be carried out in the presence or absence of a cytokine antagonist and/or a growth factor. A presence of the cytokine antagonist and/or the growth factor is preferred.

These different agents may be administered simultaneously—in the same formulation or in different formulations—or sequentially. The pharmaceutical compositions according to the invention, that comprise only one of the two agents exosomes and corticosteroid, as well as the kit according to the invention, may thus be intended for simultaneous administration on the one hand and for sequential administration of the exosomes and the corticosteroid on the other hand. Simultaneous administration however is preferred, particularly in only one formulation. This way the two pharmaceutical compositions of the kit according to the invention may be mixed in an appropriate ratio before being administered to the patient and may then be administered as a formulation. When sequentially administering the exosomes and the corticosteroid, the different agents are preferably administered within a time period of one week, preferably within 5 days, 3 days, one day or within 12 hours.

In the pharmaceutical compositions according to the invention comprising exosomes and/or a corticosteroid, a cytokine antagonist and/or a growth factor may be present or absent. The presence of the cytokine antagonist and/or the growth factor is preferred. This is because there is a clearly advantageous effect on the efficacy, particularly the long-term efficacy, of the corticosteroids in joint and spinal diseases if a cytokine antagonist such as Orthokine (natural IL-1Ra) and Anakinra (recombinant IL-1Ra) is additionally administered, particularly when the therapeutic agents are administered directly into the joint to be treated. A similar, surprisingly good efficacy of the combination of these agents was observed in autoimmune diseases, wherein especially the anti-inflammatory effect plays a role. The efficacy of a combination therapy with corticosteroids and exosomes in joint and spinal diseases such as osteoarthritis, arthritis and degenerative spinal disease is also significantly improved by additional administration of a cytokine antagonist. In a treatment with the recombinant IL-1Ra Anakinra an effect surprisingly only arises by combining it with a corticosteroid. In the natural IL-1Ra Orthokine a significant improvement of efficacy can be observed especially in inflammatory diseases. A possible explanation for this fact is that the cytokine antagonists have an anabolic effect and can neutralize or even reverse the known harmful catabolic effect of the corticosteroid in the affected joints. Thus, in the treatment of for example osteoarthritis, the corticosteroids can, apart from the cytokine antagonists, be alternatively or additionally combined with anabolic growth factors in order to achieve a similar effect. Generally the cytokine antagonist may be replaced by a growth factor or be combined with a growth factor.

The pharmaceutical composition according to the invention (according to the fourth aspect of the present invention) comprising a cytokine antagonist and/or a growth factor for use in a combination therapy together with a corticosteroid and exosomes may on the one hand be intended for simultaneous administration and on the other hand for sequential administration of the cytokine antagonist and/or growth factor, the exosomes and the corticosteroids. Simultaneous administration is preferred, particularly in just one formulation. For example the cytokine antagonist and/or growth factor may be mixed in an appropriate ratio with a corticosteroid and exosomes before administration to the patient and may then be administered as one formulation. Alternatively, in the case of simultaneous administration, the cytokine antagonist and/or growth factor, the exosomes or the corticosteroid may also be administered separately and the other components may be mixed as one formulation. However, cytokine antagonist and/or growth factor, exosomes and corticosteroid may also be administered sequentially in any order, or one of these agents may be administered at a different point in time than the two others. In sequential administration, the different agents are preferably administered within a period of time of one week, preferably within 5 days, 3 days, 1 day or within 12 hours.

In the other pharmaceutical compositions according to the invention as well as in the kit according to the invention and the use according to the invention (first, second, third, fifth, sixth and seventh aspect of the present invention), the presence or absence of a cytokine antagonist in the pharmaceutical composition is possible. The presence of a cytokine antagonist is preferred. Furthermore, the combination therapy according to the invention preferably is a combination therapy together with a cytokine antagonist, particularly in those cases where a cytokine antagonist is absent (see above) from the pharmaceutical composition itself.

The cytokine antagonist used according to the invention may be any substance or any mixture of substances that reduces or inhibits at least one, preferably substantially all of the biological activities of one or more cytokines in the body of the patient. The antagonistic effect may occur directly by the antagonist or indirectly, e.g. by activating or inhibiting further signaling pathways that also have an effect on the biologic activity of the cytokine. Preferably the biological activity of the cytokine is inhibited by blocking its interaction with one or more receptors to which it can bind. This can be achieved for example by competitive binding of the antagonist to the corresponding receptor(s) or by binding of the antagonist to the cytokine itself. Preferably the cytokine antagonist inhibits the effect of the cytokine IL-1.

The cytokine may be e.g. a protein, a peptide, a nucleic acid, a lipid or an organic compound. The cytokine antagonist may also consist of a mixture of two or more cytokine antagonists as described herein. In particular the cytokine antagonist may be a naturally occurring peptide or protein or also a recombinantly prepared peptide or protein. Furthermore the cytokine antagonist may be or comprise an antibody or antigen-binding fragment of an antibody, particularly an antibody or antibody fragment which can bind the respective cytokine or a cytokine receptor. Examples for suitable cytokine antagonists are interleukin antagonists, particularly IL-1 antagonists like IL-1Ra, tumor necrosis factor (TNF) antagonists, particularly a TNF-α antagonist such as an anti-TNF-α antibody, interferon antagonists and chemokine antagonists. Particularly preferred is naturally occurring or recombinant IL-1Ra protein, preferably human IL-1Ra. IL-1Ra preferably comprises or preferably consists of the amino acid sequence of an isoform or a homologue of the human IL-1Ra according to SEQ ID NOs: 1, 2, 3, 4 or 5, an isoform of the equine IL-1Ra according to SEQ ID NOs: 6 or 7 or an isoform of the canine IL-1Ra according to SEQ ID NO: 8.

Furthermore, according to the invention, fragments or derivatives of IL-1Ra may be used as cytokine antagonist as long as they can exercise the desired function, i.e. the reduction or inhibition of one or more biological functions of IL-1. Fragments of IL-1Ra preferably comprise at least 20, more preferably at least 40, 60, 80 or at least 100 amino acids of a natural IL-1Ra sequence. Preferably the fragments are naturally occurring secreted fragments of IL-1Ra. In one embodiment, the IL-1Ra comprises amino acids 26 to 177 of the human IL-1 Ra, preferably amino acids 26 to 177 of the sequence according to SEQ ID NO: 1. Derivates of IL-1Ra are preferably homologous to natural IL-1Ra and preferably have a homology or identity to natural IL-1Ra of at least 60%, more preferably at least 70%, 75%, 80%, 85%, 90%, 95% and most preferably at least 98% over an area of at least 20 contiguous amino acids, preferably at least 40, 60, 80 or at least 100 contiguous amino acids and most preferably over the total length of IL-1Ra. Particularly preferred is the IL-1Ra isolated from natural biological samples like blood, also called Orthokine, as well as the IL-1Ra fragment having amino acids 26 to 177 of human IL-1Ra, also called Anakinra. The preparation of Orthokine is described inter alia in Patent Application Nos. WO 00/46249 A1 and WO 03/080122 A1. Anakinra as well as further IL-1 antagonists that may be used in this invention are described inter alia in Patent Application EP 0 343 684 A1.

In the preparation of IL-1Ra from natural biological samples such as blood, like e.g. Orthokine, the obtained IL-1Ra solution preferably also contains growth factors. Thus, according to the invention, a cytokine antagonist may also be present in combination with one or more growth factors or be replaced by one or more growth factors. The growth factor according to the invention preferably has an anabolic effect. Examples for suitable growth factors are TGF-β, IGF, BMP, HGF and VEGF. Also comprised are analogues, derivatives and fragments of these growth factors as long as they have the desired effect, i.e. particularly their effect as growth factor.

The corticosteroid used according to the invention may be any naturally occurring as well as synthetically prepared corticosteroid. It may particularly be a glucocorticoid, a mineralcorticoid or an androgen, wherein glucocorticoids are preferably used. A mixture from two or more corticosteroids as described herein may also be used. Examples for glucocorticoids are cortisone, hydrocortisone, prednisone, prednisolone, cloprednol, deflazacort, fluocortin, triamcinolone, dexamethasone, methylprednisolone, fluprednisolone, clocortolone, clobetasone, alclometasone, flumethasone, fluoprednidene, fluorandrenolone, betamethasone, beclomethasone, fluocortolone, mometasone, fluticasone, halomethasone, fluocinolone, diflorasone, desoximethasone, fluocinonide, amcinonide, halcinonide, diflucortolone, clobetasol and paramethasone. Examples for mineralcorticoids are aldosterone, deoxycorticosterone and fludrocortisone, and examples for androgens are dehydroepiandrosterone (DHEA) and estrogens. The corticosteroid may be used as a free compound or in the form of a salt, ester or prodrug. In preferred embodiments the corticosteroid used is triamcinolone, cortisone, hydrocortisone, prednisolone or prednisone.

The exosomes in the pharmaceutical compositions according to the invention containing exosomes or in the kit according to the invention are preferably preparable by means of a method comprising the following steps: providing a blood sample containing exosomes and preferably concentrating the exosomes. The concentration is preferably carried out by means of a centrifugation step with at least 100,000 g, as such high centrifugal forces are especially suitable for concentrating exosomes. This step is preferably carried out for at least 30 min, particularly at least 60 min, as this way, increasing the concentration is especially effective.

The step of providing a blood sample containing exosomes preferably comprises the steps: providing a blood sample taken from a patient, optionally adding an additive promoting the formation of exosomes and incubating the blood sample in a vessel suitable for the preparation of exosomes. The incubation leads to the formation of a conditioned blood composition. Vessels suitable for the preparation of exosomes are for example syringes, tubes such as vacuum tubes, microtitre plates and transfusion bag. The surface for contacting the blood sample in vessels suitable for preparing exosomes preferably comprises glass, plastics (e.g. polystyrene, polyvinylchloride, polyethylene or polypropylene), corundum or quartz and preferably consists of one of those materials. Preferably additives enlarging the surface made of glass, plastics, corundum or quartz such as spheres, gels, wool, flour, granules or particles are added into these vessels for the preparation of exosomes. The additive promoting the formation of exosomes is preferably IL-1Ra. The additive promoting the formation of exosomes is preferably used in an amount of 1 to 20 µg per ml whole blood.

A rule that applies to the pharmaceutical compositions according to the invention for use in a combination therapy together with exosomes is that the exosomes were preferably obtained from a blood sample. The exosomes are preferably autologous or allogeneic in relation to the patient to be treated. Regarding the preparation of the exosomes reference is made to the description above for the preparation of exosomes. The centrifugation step using at least 100,000 g (preferably at least 30 min, particularly at least 60 min) described above is preferably carried out in the treatment of diseases where a high concentration of exosomes is reasonable, preferably in the treatment of rheumatoid arthritis. It is particularly preferred that such a centrifugation step is carried out generally in case the combination therapy involves exosomes obtained from a patient's blood sample.

The above detailed description for the preparation of exosomes applies mutatis mutandis to the method according to the invention for preparing a pharmaceutical composition containing a corticosteroid and exosomes comprising the steps: Providing a blood sample containing exosomes, preferably concentrating the exosomes and mixing with a corticosteroid. The mixing may be carried out in any manner known to the person skilled in the art.

In preferred embodiments the pharmaceutical compositions according to the invention and/or the kit according to the invention are intended for use in the treatment of joint diseases such as osteoarthritis, arthritis, joint inflammation and inflammatory loss of cartilage, degenerative spinal diseases, joint pain and also autoimmune diseases. The osteoarthritis to be treated may be caused by excess strain, have congenital or traumatic causes or be the result of another disease such as an inflammation. The osteoarthritis to be treated is preferably an activated osteoarthritis or an inflammatory osteoarthritis. The pharmaceutical compositions according to the invention may be used in the treatment of osteoarthritis and arthritis in any joint like for example knee joint, hip joint, ankle joint, shoulder joint, vertebral joints, finger joints, cubital joint, toe joints, temporomandibular joint and wrist joint. The arthritis to be treated may be an arthritis caused by an infection such as bacterial arthritis or an arthritis not caused by an infection such as rheumatoid arthritis, psoriatic arthritis or gouty arthritis. Alternatively the pharmaceutical composition according to the invention and/or the kit according to the invention may also be intended for the use in the treatment of a disease different from one or more of the mentioned diseases (e.g. rheumatoid arthritis). The degenerative spinal disease to be treated may be a herniated disc for example. Autoimmune diseases comprise inter alia autoimmune diseases of the joints like for example Morbus Bechterew, rheumatoid arthritis and systemic lupus erythematodes as well as other autoimmune diseases like particularly neurodermitis and alopecia areata.

The pharmaceutical compositions according to the invention and/or the kit according to the invention are preferably suitable for local administration. They are preferably intended for local administration. Thus in preferred embodiments they are intended for injection, particularly injection into the body region to be treated, particularly into the affected joint, into the affected nerve root or into the affected disc or into the local environment thereof. The pharmaceutical composition is thus particularly intended for intraarticular and/or periradicular injection. Alternatively the pharmaceutical compositions according to the invention may be formulated for topical administration, particularly as a cream or gel or for systemic administration, particularly oral administration in the form of tablets, capsules or pastilles. The type of administration depends inter alia on the disease to be treated. In local osteoarthritis or degenerative spinal disease, local administration of the pharmaceutical compositions according to the invention is preferred. In preferred embodiments the pharmaceutical compositions according to the invention and/or the kit according to the invention are exclusively intended or suitable for an administration different from systemic administration.

The pharmaceutical compositions according to the invention are suitably formulated for the different types of administration in a manner known to the person skilled in the art. Thus a pharmaceutical composition suitable for injection preferably has the form of a solution or dispersion or also a dry form e.g. as a powder or lyophilisate, which must be dissolved in an appropriate solvent such as water before the injection. The pharmaceutical compositions according to the invention contain the exosomes and/or the corticosteroid in therapeutically effective amounts. The corticosteroid preferably has a concentration of 1 to 80 mg/dose, more preferably 5 to 40 mg/dose in the pharmaceutical compositions containing the corticosteroid. A cytokine antagonist, if present, is preferably present in a concentration of 0.5 to 150 mg/dose in the pharmaceutical composition containing the cytokine antagonist but may also exist in a significantly lower concentration such as 1 ng/dose or more, for example between 1 and 1000 ng/dose. The low dose concentrations may be used in particular in a combination with growth factors and/or in natural IL-1Ra preparations such as for example compositions with Orthokine. The higher dose concentrations are for example preferred in recombinantly prepared cytokine antagonists such as Anakinra. Furthermore the pharmaceutical compositions according to the invention may furthermore contain one or more carriers and/or one or more excipients.

The pharmaceutical compositions of the invention may also be intended for a treatment of patients who had already undergone another treatment of the relevant disease, i.e. for example osteoarthritis, arthritis and/or degenerative spinal disease, particularly if this other treatment was not successful or the disease's symptoms at least partially returned after an initially successful treatment. In preferred embodiments this other treatment is a therapy with exosomes but without a corticosteroid, or a therapy with a corticosteroid, especially a glucocorticoid as described above, but without exosomes.

Patients in the sense of the invention may be humans or animals suffering from one of the diseases described herein. Thus the pharmaceutical compositions according to the invention may be suitable for treatment of a human and/or an animal like for example a dog, a cat, a horse, a cow, a pig, a goat or a camel or similar.

BRIEF DESCRIPTION OF THE FIGURES

FIG. 1A shows the dermatological changes at both feet immediately before the treatment with exosomes and triamcinolone.

FIG. 1B shows the condition of the right foot one week after treatment.

FIG. 1C shows the condition of the left foot one week after treatment.

DETAILED DESCRIPTION OF PREFERRED EMBODIMENTS

Examples

Figure 1:
FIG. 1A to FIG. 1C show pictures of the feet of a neurodermitis patient whose case is described below as case IX (Example 4).
Figure 1:
Figure 1:
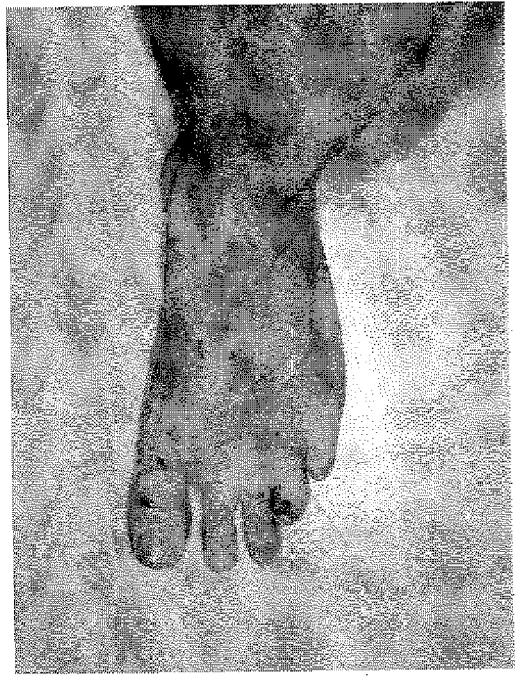

In the following, different case studies of patients with advanced osteoarthritis are described. These were treated with a combination therapy including a cytokine antagonist (e.g. recombinant IL-1Ra or IL-1Ra obtained from autologous blood samples) and a corticosteroid.

ABBREVIATIONS ri right
le left
ab ambilateral
IRO inner rotation
ORO outer rotation
VAS visual analogue scale for sensation of pain (0 to 10)
WOMAC Patient questionnaire regarding osteoarthritis
CRP c-reactive protein, an inflammation marker traceable in blood
CFJ coxofemoral joint
  Therapy with Orthokine and Cortisone in Osteoarthritis:
Number of patients: N=129
Average checkup period of time: 3 months
Average pain reduction: 71% (i.e. reduction of 100% pain before treatment to 29% after treatment)
Remarkably rapid onset of effect
  1. Local Administration of Anakinra and Cortisone and Exosomes
  Case I: T., 56 Years, Female
Diagnosis: Clinically radiologically there is medial and retropatellar gonarthrosis le, degree IV. Externally a total knee replacement le was already planned.
Therapy: 3 injections of exosomes combined with Anakinra and 10 mg triamcinolone into the left knee (twice weekly) in order to avoid knee surgery
Result: At the time of the $3^{rd}$ injection 100% pain improvement, clear functional improvement. Surgery was cancelled, patient was still pain free 5 months after the end of the therapy
  2. Local Administration of Anakinra and Cortisone and Orthokine
  Case II: L., 57 Years, Male
Diagnosis: Strong shoulder pain le for 6 months (VAS 8); since then markedly disturbed sleep. Patient could hardly sleep during the last 6 months, hence also disturbed sense of well-being. Numerous injections with cortisone into the left shoulder were without success. Surgery appointment for the left shoulder was made. Here it should be tried to avoid surgery. Radiological and clinical signs of a partial rotator cuff rupture and subacromial constriction with complete shoulder stiffness le; Unpleasant sensations left arm with weakness of strength of hand and forearm left, degree 4.
Therapy: The injections were administered dorsally and laterally into the left shoulder. 2 ml Orthokine were administered into the shoulder with 10 mg Anakinra and 10 mg triamcinolone via a syringe. The therapy was carried out on 4 consecutive days.
Result: Already on the $2^{nd}$ treatment day the patient indicated an extreme improvement of pain with a pain reduction of 90%. VAS fell from 8 to 1, the shoulder was free and normally moveable. The patient was able to sleep through the night for the first time in 6 months. The patient thus experienced a clear improvement in his well-being. The therapy was continued until day 4. There was still an unchanged clear improvement as on treatment day 2, the checkup 6 months after the treatment revealed an unchanged positive finding. Surgery was cancelled, mobility was free, the patient can lift suitcases and books above shoulder height again without problems.
  Case III: F., 45 Years, Female
Diagnosis: Complete stiffness of the shoulder ri for approx. 8 months. All previous therapies were without success, surgery was planned. The patient wanted to try another conservative treatment. Sleep at night had not been possible for several weeks. Beginning shoulder pain on the left, main finding was however the right shoulder which had VAS 9 with severe acute attacks up to 10, thus in total reduced general health.
Therapy: Treatment of the right shoulder with a combination of 2 ml Orthokine administered separately together with another syringe with a combination of 150 mg Anakinra and 5 mg triamcinolone on 6 consecutive days.
Result: 85% pain improvement from the $5^{th}$ day. Sleeping through the night was possible since the $2^{nd}$ treatment, thus significantly improved general health. VAS at the end of the treatment at the first checkup 8 months after the treatment still showed a very good unchanged result; surgery was cancelled.

3. Exosomes Incubated with IL-1Ra and Triamcinolone/Prednisolone

Case IV: S., 25 Years, Male

Diagnosis: Severe juvenile rheumatoid arthritis since approx. 15 years. Treatment with 25 mg Enbrel 2×weekly, 10 mg methotrexate, 5 mg decortin and naproxen 2×1 per day. Massive synovitis and pain both CFJ and both shoulders. Abduction 60 degrees of both shoulders before treatment. Laboratory CRP value: 5.35 (normal value: 0.5 mg); leukocytosis.

Therapy: Blood was taken for preparing exosomes in a 6 ml syringe (Orthokine syringe). Then 24 h incubation at 37 degrees, wherein when filling the syringe with blood, 1 mg Anakinra (IL-1Ra) and 2 mg prednisolone were given into the syringe beforehand. After several steps of centrifugation (up to 100 000 g) the mixture was then administered into patient's CFJs and the shoulders.

Result: After 3 days beginning significantly reduced swelling of the joints. Clinical and chemical checkup after 9 days: 80% pain improvement, CFJ normal, no swelling. CRP value now 1.93. Improvement also in other affected joints which were not locally injected. General quality of life was significantly improved. At the checkup after 3 months the situation remains stable. VAS 9 before treatment, since the first week after injection VAS 3. Patient very satisfied, can continue his work.

4. Injection with Exosomes and Additional Triamcinolone in Injection

Case V: M., 64 Years, Female

Severe therapy-resistant rheumatoid arthritis despite basic therapy with prednisolone 15 mg p.d., Lantarel 20 mg p.w., Humira every 2 weeks. Radiation synovectomy into the wrists only showed a minimal effect, intraarticular injections in doses between 10 mg to 40 mg triamcinolone only showed a weak (20% pain improvement after one week) effect on the pain as well as on the inflammation parameters. When presenting for exosome therapy CRP 120 mg/l despite basic therapy described above, very strong pain in the hands and both shoulders. Injection of exosomes (after incubation with IL-1Ra) and admixing total amount of 20 mg triamcinolone in MCP2-5 ab. and both shoulders. Afterwards clinically strong improvement (80% pain reduction after 1 week) starting after 2 days, which continually lasts for 3 months. CRP checkup after 3 months CRP 42.6 mg/l, basic therapy unchanged so that the effect must be attributed to the combination of exosomes with triamcinolone. Higher doses of only triamcinolone as described above did not show comparable effects.

Case VI: M., 25 Years, Male

Known psoriasic arthritis; basic therapy 5 mg prednisolone and 10 mg MTX; main problem under basic therapy still clear swelling left knee with synovitis and swelling of 2 cm compared with the opposite side. Additional swelling in the area of the wrists despite basic therapy. Intraarticular cortisone injections into the knee and wrists with a dose of between 20-40 mg only showed a very weak effect for some days with pain reduction of 10-30%. Presenting for exosome therapy. CRP immediately before injection 5.6 mg/l. After preparing exosomes application of exosomes (prepared after IL-1Ra incubation as described) into the left knee (exosomes+triamcinolone 10 mg) and in the MCP 2+3 ab (exosomes with 2 mg triamcinolone respectively per joint). Uneventful course, after a few days clear reduction of pain of 90%; CRP after 3 months 3.0 mg/l; knee swelling completely gone after 1 week, no difference between left and right: 5 mg prednisolone could be discontinued completely, as the effect from the intraarticular injection of exosomes and triamcinolone was continuous.

Case VII: R., 32 Years, Male

Complete alopecia known for years, all therapy attempts incl. systemic and local application of cortisone in high systemic and local doses (10-80 mg prednisolone) without effect: presenting for treatment with exosomes. Preparation of the exosomes with the technique described above, one-time intramuscular injection of the exosomes together with 10 mg triamcinolone. Follow-up normal, after 3 months detection of hair growth in approximately half of the area originally haired before affection.

Case VIII: H., 47 Years, Male:

Gonarthrosis ri with cartilage defects verified arthroscopically degree 2-4 according to Outerbridge. The patient wishes to delay surgery and joint replacement. History of intraarticular injection of triamcinolone in doses of 10-40 mg to no effect. Injection of 1 ml of exosomes prepared by means of the technique as described after incubation with IL-1Ra. One-time intraarticular injection of 2 ml of exosomes, after 4 weeks patient dissatisfied with clinical effect regarding pain and function. Afterwards decision for an intraarticular injection into the right knee combined with 10 mg triamcinolone. Uneventful course. After 1 week 95% pain improvement, function completely restored, patient can participate in a tennis match for the first time in years.

Case IX: J., 27 Years, Male:

Severe dermatologically verified neurodermitis with strong changes, especially in the area of hands and feet. All known dermatologic therapies did not show, any sustained improvement, in particular only a short-term effect of 1 week after local application of corticosteroids and systemic intramuscular application of prednisolone and triamcinolone in doses of 80 mg could be observed. Preparation of exosomes according to the technique described, intramuscular application; after 3 weeks no satisfying effect on the skin changes and the disease. After that, attempt of intramuscular application of 2 ml of exosomes in connection with 20 mg triamcinolone. Within 2 weeks clear improvement staying the same for over 6 months. Subsequent slight deterioration but still improvement compared to preliminary findings. FIG. 1A describes the dermatological changes at both feet immediately before treatment, FIG. 1B and FIG. 1C one week after treatment for the right/left foot.

Case X, B., 69 Years, Female

Severe Bechterew arthritis with iridocyclitis left eye. Patient is given prednisolone and MTX in changing doses as basic therapy. CRP 20_3 mg/l; left CFJ clearly swollen with +2 cm compared to the other side; left MCP and first knuckle $1^{st}$ finger left clearly swollen and painful, right shoulder swollen, painful, abduction reduced by 30 degrees compared to normal. Subsequent injection of exosomes according to the known technique into the affected joints without pain reduction and CRP reduction, subsequent injection of triamcinolone in a total dose of 40 mg into all affected joints, slight improvement of 20% for 1 week. After 4 weeks injection of exosomes and triamcinolone total dose 20 mg, after that 80% improvement of shoulder, fingers 50% improvement with reduced swelling of 8.2 cm left thumb circumference MCP joint to 6.6 cm. No clear effect yet on ankle. CRP within 1 week reduced from 20.3 mg/l to 2.9 mg/l.

What is claimed is:

1. A pharmaceutical composition comprising a glucocorticoid together with exosomes in the presence or absence of a cytokine antagonist and/or a growth factor, wherein the exosomes are obtained from blood and the glucocorticoid is one or more selected from the group consisting of, prednisone, prednisolone, cloprednol, deflazacort, fluocortin, triamcinolone, dexamethasone, methylprednisolone, fluprednisolone, clocortolone, clobetasone, alclomethasone, flumethasone, fluoprednidene, fluorandrenolone, betamethasone, beclomethasone, fluocortolone, mometasone, fluticasone, halomethasone, fluocinolone, diflorasone, desoximethasone, fluocinonide, amcinonide, halcinonide, diflucortolone, clobetasol, paramethasone, and a salt, ester or prodrug thereof.

2. A pharmaceutical composition comprising a glucocorticoid together with exosomes in the presence or absence of a cytokine antagonist and/or a growth factor, wherein the exosomes are obtained from blood and the glucocorticoid is triamcinolone or a salt, ester or prodrug thereof.

3. The pharmaceutical composition according to claim 2, wherein the glucocorticoid is present in a concentration of 1 to 80 mg/dose in the pharmaceutical composition containing the glucocorticoid.

4. The pharmaceutical composition according to claim 2, wherein the exosomes are obtained by a method comprising the steps of: providing a blood sample containing exosomes and optionally concentrating the exosomes.

5. The pharmaceutical composition according to claim 2, wherein the exosomes are autologous or allogeneic.

6. The pharmaceutical composition according to claim 2 for the treatment of joint diseases, degenerative spinal diseases and/or joint pain.

7. The pharmaceutical composition according to claim 6, wherein the joint disease is an activated osteoarthritis or an inflammatory osteoarthritis.

8. The pharmaceutical composition according to claim 6, wherein the degenerative spinal disease is a herniated disc.

9. The pharmaceutical composition according to claim 2 for treatment of an autoimmune disease.

10. The pharmaceutical composition according to claim 9, wherein the autoimmune disease is neurodermitis or alopecia areata.

11. The pharmaceutical composition according to claim 2, wherein the pharmaceutical composition is suitable for local administration.

12. The pharmaceutical composition according to claim 11, wherein the local administration is selected from the group consisting of injection into the affected body region, or into the local environment thereof, intra-articular injection, and topical administration.

13. The pharmaceutical composition according to claim 2, wherein the pharmaceutical composition further contains a carrier and/or an excipient.

14. The pharmaceutical composition according to claim 2, wherein a cytokine antagonist is present and the cytokine antagonist is selected from the group consisting of interleukin antagonists, tumor necrosis factor antagonists, interferon antagonists and chemokine antagonists.

15. The pharmaceutical composition according to claim 14, wherein the cytokine antagonist is naturally occurring or recombinant IL-1 Ra protein.

16. The pharmaceutical composition according to claim 14, wherein the cytokine antagonist is present in a concentration of 0.5 to 150 mg/dose in the pharmaceutical composition containing the cytokine antagonist.

17. The pharmaceutical composition according to claim 2, wherein a growth factor is present and the growth factor is selected from the group consisting of TGF-β, IGF, BMP, HGF and VEGF.

18. The pharmaceutical composition according to claim 6, wherein the joint disease is selected from the group consisting of, osteoarthritis, arthritis, joint inflammation and inflammatory loss of cartilage.

19. The pharmaceutical composition according to claim 18, wherein the arthritis is an arthritis caused by an infection.

20. The pharmaceutical composition according to claim 19, wherein the arthritis caused by an infection is bacterial arthritis.

21. The pharmaceutical composition according to claim 14, wherein the interleukin antagonist is an IL-1 antagonist and/or the tumour necrosis factor antagonist is a TNF-α antagonist.

22. The pharmaceutical composition according to claim 21, wherein the IL-1 antagonist is IL-1 Ra and/or the TNF-α antagonist is an anti-TNF-α antagonist.

23. The pharmaceutical composition according to claim 12, wherein the injection into the affected body region is selected from the group consisting of an injection into the affected joint, an injection into the affected nerve root, an injection into the affected intervertebral disc and an injection into the local environment thereof.

24. The pharmaceutical composition according to claim 15, wherein the naturally occurring IL-1 Ra protein is autologous serum in which the IL-1 Ra is enriched and/or the recombinant IL-1 Ra protein is anakinra.

25. A kit comprising (i) a pharmaceutical composition comprising exosomes in the presence or absence of a cytokine antagonist and/or a growth factor and (ii) a pharmaceutical composition comprising a glucocorticoid in the presence or absence of a cytokine antagonist and/or a growth factor, wherein the exosomes are obtained from blood and the glucocorticoid is triamcinolone or a salt, ester or prodrug thereof.

26. A method for the preparation of a pharmaceutical composition containing a glucocorticoid and exosomes comprising the steps: providing a blood sample containing exosomes, optionally concentrating the exosomes and mixing with said glucocorticoid, wherein the glucocorticoid is triamcinolone or a salt, ester or prodrug thereof.

27. A method for the preparation of a pharmaceutical composition containing a glucocorticoid and exosomes comprising the steps: providing a blood sample containing exosomes, optionally concentrating the exosomes, and mixing with said glucocorticoid, wherein said glucocorticoid is one or more selected from the group consisting of, prednisone, prednisolone, cloprednol, deflazacort, fluocortin, triamcinolone, dexamethasone, methylprednisolone, fluprednisolone, clocortolone, clobetasone, alclomethasone, flumethasone, fluoprednidene, fluorandrenolone, betamethasone, beclomethasone, fluocortolone, mometasone, fluticasone, halomethasone, fluocinolone, diflorasone, desoximethasone, fluocinonide, amcinonide, halcinonide, diflucortolone, clobetasol, paramethasone and a salt, ester or prodrug thereof.

28. The pharmaceutical composition according to claim 19, wherein the arthritis is not caused by an infection and is selected from the group consisting of rheumatoid arthritis, psoriatic arthritis and gouty arthritis.

* * * * *

SEQUENCE LISTING

<160> NUMBER OF SEQ ID NOS: 8

<210> SEQ ID NO 1
<211> LENGTH: 177
<212> TYPE: PRT
<213> ORGANISM: Homo sapiens

<400> SEQUENCE: 1

Met Glu Ile Cys Arg Gly Leu Arg Ser His Leu Ile Thr Leu Leu Leu
1               5                   10                  15

Phe Leu Phe His Ser Glu Thr Ile Cys Arg Pro Ser Gly Arg Lys Ser
            20                  25                  30

Ser Lys Met Gln Ala Phe Arg Ile Trp Asp Val Asn Gln Lys Thr Phe
        35                  40                  45

Tyr Leu Arg Asn Asn Gln Leu Val Ala Gly Tyr Leu Gln Gly Pro Asn
    50                  55                  60

Val Asn Leu Glu Glu Lys Ile Asp Val Val Pro Ile Glu Pro His Ala
65                  70                  75                  80

Leu Phe Leu Gly Ile His Gly Gly Lys Met Cys Leu Ser Cys Val Lys
                85                  90                  95

Ser Gly Asp Glu Thr Arg Leu Gln Leu Glu Ala Val Asn Ile Thr Asp
            100                 105                 110

Leu Ser Glu Asn Arg Lys Gln Asp Lys Arg Phe Ala Phe Ile Arg Ser
        115                 120                 125

Asp Ser Gly Pro Thr Thr Ser Phe Glu Ser Ala Ala Cys Pro Gly Trp
    130                 135                 140

Phe Leu Cys Thr Ala Met Glu Ala Asp Gln Pro Val Ser Leu Thr Asn
145                 150                 155                 160

Met Pro Asp Glu Gly Val Met Val Thr Lys Phe Tyr Phe Gln Glu Asp
                165                 170                 175

Glu

<210> SEQ ID NO 2
<211> LENGTH: 159
<212> TYPE: PRT
<213> ORGANISM: Homo sapiens

<400> SEQUENCE: 2

Met Ala Leu Glu Thr Ile Cys Arg Pro Ser Gly Arg Lys Ser Ser Lys
1               5                   10                  15

Met Gln Ala Phe Arg Ile Trp Asp Val Asn Gln Lys Thr Phe Tyr Leu
            20                  25                  30

Arg Asn Asn Gln Leu Val Ala Gly Tyr Leu Gln Gly Pro Asn Val Asn
        35                  40                  45

Leu Glu Glu Lys Ile Asp Val Val Pro Ile Glu Pro His Ala Leu Phe
    50                  55                  60

Leu Gly Ile His Gly Gly Lys Met Cys Leu Ser Cys Val Lys Ser Gly
65                  70                  75                  80

Asp Glu Thr Arg Leu Gln Leu Glu Ala Val Asn Ile Thr Asp Leu Ser
                85                  90                  95

Glu Asn Arg Lys Gln Asp Lys Arg Phe Ala Phe Ile Arg Ser Asp Ser
            100                 105                 110

Gly Pro Thr Thr Ser Phe Glu Ser Ala Ala Cys Pro Gly Trp Phe Leu
        115                 120                 125

Cys Thr Ala Met Glu Ala Asp Gln Pro Val Ser Leu Thr Asn Met Pro
    130                 135                 140

```
Asp Glu Gly Val Met Val Thr Lys Phe Tyr Phe Gln Glu Asp Glu
145                 150                 155
```

<210> SEQ ID NO 3
<211> LENGTH: 180
<212> TYPE: PRT
<213> ORGANISM: Homo sapiens

<400> SEQUENCE: 3

```
Met Ala Leu Ala Asp Leu Tyr Glu Glu Gly Gly Gly Gly Gly Glu
1               5                   10                  15

Gly Glu Asp Asn Ala Asp Ser Lys Glu Thr Ile Cys Arg Pro Ser Gly
            20                  25                  30

Arg Lys Ser Ser Lys Met Gln Ala Phe Arg Ile Trp Asp Val Asn Gln
                35                  40                  45

Lys Thr Phe Tyr Leu Arg Asn Asn Gln Leu Val Ala Gly Tyr Leu Gln
    50                  55                  60

Gly Pro Asn Val Asn Leu Glu Glu Lys Ile Asp Val Val Pro Ile Glu
65                  70                  75                  80

Pro His Ala Leu Phe Leu Gly Ile His Gly Gly Lys Met Cys Leu Ser
                85                  90                  95

Cys Val Lys Ser Gly Asp Glu Thr Arg Leu Gln Leu Glu Ala Val Asn
                100                 105                 110

Ile Thr Asp Leu Ser Glu Asn Arg Lys Gln Asp Lys Arg Phe Ala Phe
                115                 120                 125

Ile Arg Ser Asp Ser Gly Pro Thr Thr Ser Phe Glu Ser Ala Ala Cys
130                 135                 140

Pro Gly Trp Phe Leu Cys Thr Ala Met Glu Ala Asp Gln Pro Val Ser
145                 150                 155                 160

Leu Thr Asn Met Pro Asp Glu Gly Val Met Val Thr Lys Phe Tyr Phe
                165                 170                 175

Gln Glu Asp Glu
            180
```

<210> SEQ ID NO 4
<211> LENGTH: 143
<212> TYPE: PRT
<213> ORGANISM: Homo sapiens

<400> SEQUENCE: 4

```
Met Gln Ala Phe Arg Ile Trp Asp Val Asn Gln Lys Thr Phe Tyr Leu
1               5                   10                  15

Arg Asn Asn Gln Leu Val Ala Gly Tyr Leu Gln Gly Pro Asn Val Asn
            20                  25                  30

Leu Glu Glu Lys Ile Asp Val Pro Ile Glu Pro His Ala Leu Phe
            35                  40                  45

Leu Gly Ile His Gly Gly Lys Met Cys Leu Ser Cys Val Lys Ser Gly
    50                  55                  60

Asp Glu Thr Arg Leu Gln Leu Glu Ala Val Asn Ile Thr Asp Leu Ser
65                  70                  75                  80

Glu Asn Arg Lys Gln Asp Lys Arg Phe Ala Phe Ile Arg Ser Asp Ser
                85                  90                  95

Gly Pro Thr Thr Ser Phe Glu Ser Ala Ala Cys Pro Gly Trp Phe Leu
                100                 105                 110

Cys Thr Ala Met Glu Ala Asp Gln Pro Val Ser Leu Thr Asn Met Pro
            115                 120                 125
```

```
Asp Glu Gly Val Met Val Thr Lys Phe Tyr Phe Gln Glu Asp Glu
        130                 135                 140
```

<210> SEQ ID NO 5
<211> LENGTH: 155
<212> TYPE: PRT
<213> ORGANISM: Homo sapiens

<400> SEQUENCE: 5

```
Met Val Leu Ser Gly Ala Leu Cys Phe Arg Met Lys Asp Ser Ala Leu
  1               5                  10                  15

Lys Val Leu Tyr Leu His Asn Asn Gln Leu Leu Ala Gly Gly Leu His
             20                  25                  30

Ala Gly Lys Val Ile Lys Gly Glu Glu Ile Ser Val Val Pro Asn Arg
         35                  40                  45

Trp Leu Asp Ala Ser Leu Ser Pro Val Ile Leu Gly Val Gln Gly Gly
     50                  55                  60

Ser Gln Cys Leu Ser Cys Gly Val Gly Gln Pro Thr Leu Thr Leu
 65                  70                  75                  80

Glu Pro Val Asn Ile Met Glu Leu Tyr Leu Gly Ala Lys Glu Ser Lys
                 85                  90                  95

Ser Phe Thr Phe Tyr Arg Arg Asp Met Gly Leu Thr Ser Ser Phe Glu
            100                 105                 110

Ser Ala Ala Tyr Pro Gly Trp Phe Leu Cys Thr Val Pro Glu Ala Asp
        115                 120                 125

Gln Pro Val Arg Leu Thr Gln Leu Pro Glu Asn Gly Gly Trp Asn Ala
    130                 135                 140

Pro Ile Thr Asp Phe Tyr Phe Gln Gln Cys Asp
145                 150                 155
```

<210> SEQ ID NO 6
<211> LENGTH: 177
<212> TYPE: PRT
<213> ORGANISM: Equus caballus

<400> SEQUENCE: 6

```
Met Glu Ile Arg Arg Ser Val Arg His Leu Ile Ser Leu Leu Leu
  1               5                  10                  15

Phe Leu Phe Tyr Ser Glu Thr Ala Cys His Pro Leu Gly Lys Arg Pro
             20                  25                  30

Cys Lys Met Gln Ala Phe Arg Ile Trp Asp Val Asn Gln Lys Thr Phe
         35                  40                  45

Tyr Met Arg Asn Asn Gln Leu Val Ala Gly Tyr Leu Gln Glu Ser Asn
     50                  55                  60

Thr Lys Leu Gln Glu Lys Ile Asp Val Val Pro Ile Glu Pro Asp Ala
 65                  70                  75                  80

Leu Phe Leu Gly Leu His Gly Arg Lys Leu Cys Leu Ala Cys Val Lys
                 85                  90                  95

Ser Gly Asp Glu Ile Arg Phe Gln Leu Glu Ala Val Asn Ile Thr Asp
            100                 105                 110

Leu Ser Lys Asn Lys Glu Glu Asn Lys Arg Phe Thr Phe Ile Arg Ser
        115                 120                 125

Asn Ser Gly Pro Thr Thr Ser Phe Glu Ser Ala Ala Cys Pro Gly Trp
    130                 135                 140

Phe Leu Cys Thr Ala Gln Glu Ala Asp Arg Pro Val Ser Leu Thr Asn
145                 150                 155                 160
```

```
Lys Pro Lys Glu Ser Phe Met Val Thr Lys Phe Tyr Leu Gln Glu Asp
                165                 170                 175

Gln

<210> SEQ ID NO 7
<211> LENGTH: 177
<212> TYPE: PRT
<213> ORGANISM: Equus caballus

<400> SEQUENCE: 7

Met Glu Ile Arg Arg Ser Val Arg His Leu Ile Ser Leu Leu Leu
1               5                   10                  15

Phe Leu Leu Tyr Ser Glu Thr Ala Cys His Pro Leu Gly Lys Arg Pro
                20                  25                  30

Cys Lys Met Gln Ala Phe Arg Ile Trp Asp Val Asn Gln Lys Thr Phe
            35                  40                  45

Tyr Met Arg Asn Asn Gln Leu Val Ala Gly Tyr Leu Gln Glu Ser Asn
50                  55                  60

Thr Lys Leu Gln Glu Lys Ile Asp Val Val Pro Ile Glu Pro Asp Ala
65                  70                  75                  80

Leu Phe Leu Gly Leu His Gly Arg Lys Leu Cys Leu Ala Cys Val Lys
                85                  90                  95

Ser Gly Asp Glu Ile Arg Phe Gln Leu Glu Ala Val Asn Ile Thr Asp
            100                 105                 110

Leu Ser Lys Asn Lys Glu Glu Asn Lys Arg Phe Thr Phe Ile Arg Ser
        115                 120                 125

Asn Ser Gly Pro Thr Thr Ser Phe Glu Ser Ala Ala Cys Pro Gly Trp
130                 135                 140

Phe Leu Cys Thr Ala Gln Glu Ala Asp Arg Pro Val Ser Leu Thr Asn
145                 150                 155                 160

Lys Pro Lys Glu Ser Phe Met Val Thr Lys Phe Tyr Leu Gln Glu Asp
                165                 170                 175

Gln

<210> SEQ ID NO 8
<211> LENGTH: 176
<212> TYPE: PRT
<213> ORGANISM: Canis familiaris

<400> SEQUENCE: 8

Met Glu Thr Cys Arg Cys Pro Leu Ser Tyr Leu Ile Ser Phe Leu Leu
1               5                   10                  15

Phe Leu Ser His Ser Glu Thr Ala Cys Arg Pro Leu Gly Lys Arg Pro
                20                  25                  30

Cys Arg Met Gln Ala Phe Arg Ile Trp Asp Val Asn Gln Lys Thr Phe
            35                  40                  45

Tyr Leu Arg Asn Asn Gln Leu Val Ala Gly Tyr Leu Gln Gly Ser Asn
50                  55                  60

Thr Lys Leu Glu Glu Lys Leu Asp Val Val Pro Val Glu Pro His Ala
65                  70                  75                  80

Val Phe Leu Gly Ile His Gly Gly Lys Leu Cys Leu Ala Cys Val Lys
                85                  90                  95

Ser Gly Asp Glu Thr Arg Leu Gln Leu Glu Ala Val Asn Ile Thr Asp
            100                 105                 110

Leu Ser Lys Asn Lys Asp Gln Asp Lys Arg Phe Thr Phe Ile Leu Ser
```

-continued

```
            115                 120                 125
Asp Ser Gly Pro Thr Thr Ser Phe Glu Ser Ala Ala Cys Pro Gly Trp
        130                 135                 140
Phe Leu Cys Thr Ala Leu Glu Ala Asp Arg Pro Val Ser Leu Thr Asn
145                 150                 155                 160
Arg Pro Glu Glu Ala Met Met Val Thr Lys Phe Tyr Phe Gln Lys Glu
                165                 170                 175
```